United States Patent
Jenny et al.

(10) Patent No.: US 7,604,932 B2
(45) Date of Patent: Oct. 20, 2009

(54) ASSAY FOR TISSUE FACTOR IN A SAMPLE

(75) Inventors: Richard J. Jenny, Essex Junction, VT (US); Saulius Butenas, South Burlington, VT (US)

(73) Assignee: Haematologic Technologies, Inc., Essex Junction, VT (US)

( * ) Notice: Subject to any disclaimer, the term of this patent is extended or adjusted under 35 U.S.C. 154(b) by 213 days.

(21) Appl. No.: 10/534,187

(22) PCT Filed: Nov. 6, 2003

(86) PCT No.: PCT/US03/35608

§ 371 (c)(1), (2), (4) Date: Nov. 9, 2005

(87) PCT Pub. No.: WO2004/043991

PCT Pub. Date: May 27, 2004

(65) Prior Publication Data

US 2006/0148022 A1    Jul. 6, 2006

Related U.S. Application Data

(60) Provisional application No. 60/425,662, filed on Nov. 13, 2002, provisional application No. 60/466,214, filed on Apr. 28, 2003.

(51) Int. Cl.
*C12Q 1/00* (2006.01)
(52) U.S. Cl. .......................................................... 435/4
(58) Field of Classification Search .................. None
See application file for complete search history.

(56) References Cited

U.S. PATENT DOCUMENTS

| 5,399,487 | A | 3/1995 | Butenas et al. |
| 6,287,794 | B1 | 9/2001 | Safar et al. |
| 7,049,087 | B2 * | 5/2006 | Jenny et al. ................ 435/13 |

OTHER PUBLICATIONS

Butenas et al. "Synthetic substrates for human factor VIIa and factor VIIa-tissue factor" Biochem. (1993) 32: 6531-6538.*
Butenas et al. "Cooperative interaction of divalent metal ions, substrate and tissue factor with factor VIIa" Biochem. (1994) 33:3449-3456.*

* cited by examiner

*Primary Examiner*—Sandra Saucier
*Assistant Examiner*—Susan Hanley
(74) *Attorney, Agent, or Firm*—McDonnell Boehnen Hulbert & Berghoff LLP

(57) ABSTRACT

The invention provides assays for detecting and quantitating tissue factor and factor VIIa in simple and complex biological systems. The assays are performed by detecting and/or measuring the tissue factor cofactor activity and factor VIIa enzymatic activity using aminonapthalene-based fluorogenic substrates.

12 Claims, 2 Drawing Sheets

ASSAY FOR TISSUE FACTOR IN A SAMPLE

This application claims priority from U.S. Provisional Application 60/425,662, filed Nov. 6, 2002, and U.S. Provisional Application 60/466,214, filed Apr. 28, 2003, each of which is incorporated herein by reference in its entirety.

BACKGROUND OF THE INVENTION

1. Field of the Invention

The invention relates, generally, to the field of detection of proteins involved in blood coagulation. More specifically, it relates to a method for determining the amount of tissue factor and/or factor VIIa in simple and complex biological systems.

2. Description of the Related Art

Tissue factor (TF) and factor VIIa (fVIIa) are essential components for the initiation of blood coagulation. Blood coagulation is initiated when cryptic TF becomes exposed on the surface of vascular cells where it can bind circulating fVIIa.

Although several assays for fVIIa have been described (some commercially available), those assays do not discriminate between factor VII and factor VIIa, either due to the lack of specificity in immunologic methods, or due to the feedback-activation of factor VII in the amidolytic and clot-based assays. For example, there is a "direct" factor VIIa assay based upon clotting of plasma initiated with a soluble mutant of TF. The assay involves the entire coagulation cascade, so it is therefore sensitive to the concentration of procoagulant proteins and coagulation inhibitors as well as factor VII by virtue of feed-back activation. Thus, the clotting time of plasma reflects the concentration of fVIIa, as well as, the concentration of all components of plasma involved in coagulation and its regulation.

Moreover, because of the critical role TF plays in hemostasis, its potential role in metastasis, and its extensive use in-vitro, it is important to have a sensitive and specific TF assay that can detect relatively low amounts of this protein in biological fluids, cell cultures, lysates, and in purified and semi-purified systems. TF assays thus far developed employ clotting, chromogenic, and immunochemical methods. The clotting methods involve the entire coagulation cascade and are therefore sensitive to alterations in the levels of procoagulant proteins and coagulation inhibitors. Chromogenic methods do not allow a direct measure of TF activity, and are expensive since they require additional purified coagulation factors. Similarly, immunochemical methods are relatively expensive and time-consuming. Thus, at the present time, there is no quick, accurate and somewhat universal method to directly measure TF activity.

Accordingly, a functional-based assay that could be used to measure TF or fVIIa in purified and/or complex biological systems would have a variety of potential applications. These include: in-vitro diagnostics for the assessment of hemostatic potential; in-vitro diagnostics for thrombotic risk assessment; in-vitro diagnostics for cancer screening; quality control during the purification of recombinant tissue factor; quality control during the manufacture of prothrombin time PT reagents; and characterization of final TF and/or PT reagents.

It has been demonstrated that the amidolytic activity of the TF/factor VIIa complex toward small fluorogenic substrates is membrane (phospholipid) independent. This suggests that TF can be successfully quantitated in a free form in purified systems and biological fluids, as well as, present on cell or artificial membranes and in cell lysates. Fluorogenic substrates, which allow a quantitation of low concentrations of factor VIIa (as described above), will similarly allow the quantitation of low concentrations of TF. U.S. Pat. No. 5,399,487, which is fully incorporated by reference, discloses fluorogenic substrates for serine proteases that contain 6-amino-1-naphthalenesulfonamide (ANSN) leaving groups.

SUMMARY OF INVENTION

The invention provides assays for detecting and quantitating tissue factor and factor VIIa in purified form or in complex biological mixtures such as body fluids and tissues, e.g., plasma. The assay is performed by detecting and/or measuring the TF-dependent fVIIa enzymatic activity using aminonapthalene sulfonamide-based (ANSN-based) fluorogenic substrates. The TF-dependent activity is an important aspect of this assay, as the TF/factor VIIa complex will yield nearly a 100-fold higher rate of substrate hydrolysis relative to factor VIIa alone with appropriate substrates. It has been demonstrated that the properties of the ANSN-based fluorogenic substrates allow for the direct quantitation of fVIIa at low (<5) picomolar concentrations in purified systems.

The enzymatic activity of a TF/fVIIa complex is related to the concentration of either TF or fVIIa in the sample, depending upon which is present at a limiting concentration. Standard calibration curves can be generated using samples with known concentrations of TF or fVIIa. The concentration of active TF or fVIIa in a sample suspected of containing these factors can be determined by comparing the detected enzymatic activity to the calibration curves.

DETAILED DESCRIPTION OF THE INVENTION

Figure 1:
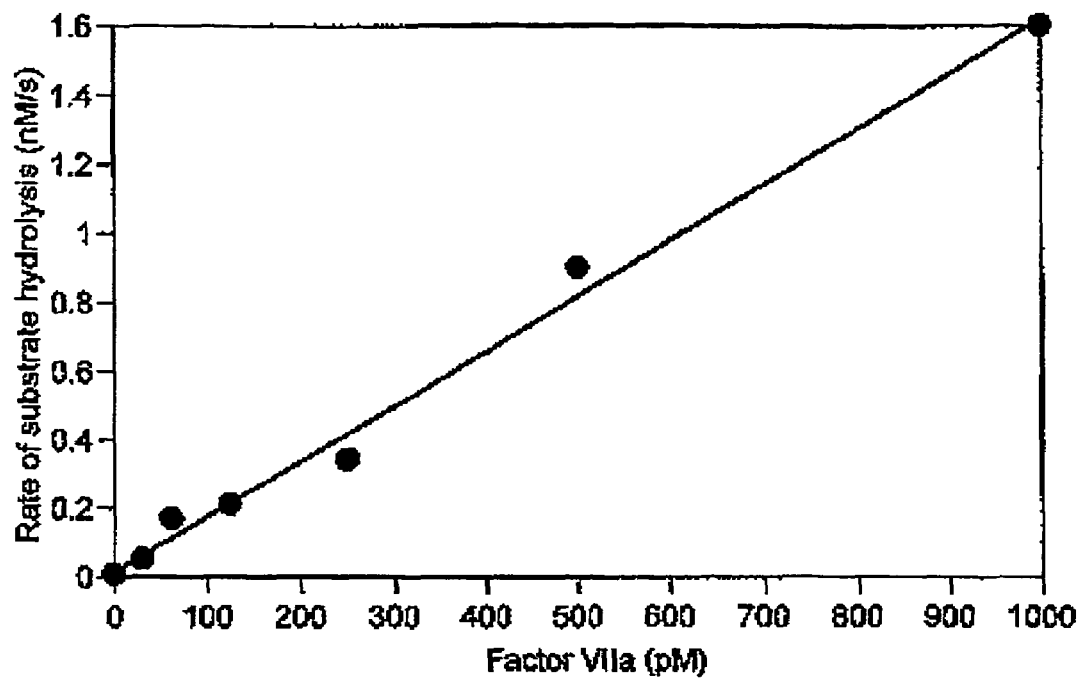
FIG. 1 is a fluorogenic assay calibration curve for factor VIIa amidolyic activity in the presence of excess (5 nM) TF.

As noted above, the invention provides assays for tissue factor and factor VIIa. There are two broad aspects of the invention.

One aspect is a method used to determine the cofactor activity of TF in a fluid sample suspected of containing TF or containing an unknown quantity of TF. The term "determine" as used herein encompasses both quantitative measurements as well as qualitative assessments. Thus, the methods of the invention can be used to determine (1) if any TF is present in a sample and (2) the amount of TF activity in a sample. In the first aspect, the assay initially involves combining the sample suspected to contain TF with fVIIa to form a TF/fVIIa complex, i.e., a reaction mixture. Optionally, added to the reaction mixture are divalent metal ions, such as calcium ion, or metal ion chelators, such as ethylenediamimetetraacetic acid (EDTA) and ethylene glycol-bis(2-aminoethylether)-N,N,N',N'-tetraacetic acid (EGTA). Other optional components of the reaction mixture include alcohols and polyhydroxylated materials. Representative alcohols include lower alcohols, e.g., $C_1$-$C_6$ alcohols such as methanol, ethanol, propanol, pentanol, and hexanol. Polyhydroxylated materials include various glycols and sugars. Representative polyhydroxylated materials include glycerol, ethylene glycol, diethylene glycol, triethylene glycol, propylene glycol, dipropylene glycol, trimethylene glycol, butylene glycols, 1,2-cyclohexanediol, poly(oxyalkylene)polyols derived from the condensation of ethylene oxide, propylene oxide, or any combination thereof, 1,1,1-trimethylolpropane, 1,1,1-trimethylolethane, 2,2-dimethyl-1,3-propane diol, and pentaerythritol. More preferably, the alcohol is ethanol or n-propanol. Preferred polyhydroxylated materials include glycerol, ethylene glycol, and propylene glycol. More preferably, the polyhydroxylated material is ethylene glycol or propylene glycol.

Typically, the TF sample is combined with a molar excess of fVIIa to produce a TF/fVIIa enzyme complex in a TF limiting manner. When developing a calibration curve, there is a possibility that fVIIa may not be present in an excess relative to the concentration of TF. If so, there will be no change in the fluorescence level with change in concentration, i.e., a flat line will be generated, until the TF concentration is reduced to a point where fVIIa is in excess. Preferably, the excess of fVIIa is about a 2-fold excess. Alternatively, the molar excess of fVIIa is about a 100-fold molar excess; in yet another alternative, the excess of fVIIa is about a 1000-fold excess. Finally, the enzymatic activity of the complex may be detected, preferably by using an amino-napthalenesulfonamide-based fluorogenic substrate. Fluorescence can be monitored (continuously or discontinuously) using a suitable fluorescence spectrophotometer. Representative devices include (a) Perkin Elmer model MPF-44A; (b) a Perkin Elmer Model LS50B; (c) a Molecular Devices Spectramax fluorescence plate reader. When an ANSN-based fluorescent substrate is used, the fluorophore is preferably detected using monochromaters set at an excitation wavelength of about 340-360 nm, preferably about 350 nm, and an emission wavelength of about 460-480 nm, preferably about 470 nm. Light scattering artifacts can be minimized using an appropriate cut-off filter in the emission light beam, e.g., a 435 nm cut off filter.

The amino-naphthalenesulfonamide (ANSN) based fluorogenic substrate used is a compound of the formula:

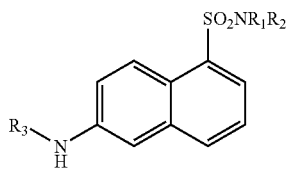

or a pharmaceutically acceptable non-toxic salts thereof; wherein $R_1$ is hydrogen, straight or branched chain lower alkyl having 1-6 carbon atoms optionally substituted with $C_1$-$C_6$ alkoxy, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylakyl where the alkyl portion has 1-6 carbon atoms, or phenylalkyl where the alkyl portion is straight or branched chain alkyl having 1-6 carbon atoms, or a group of the formula

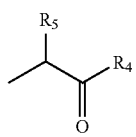

$R_5$ represents hydrogen or an amino acid side chain; and
$R_4$ is hydroxy, $C_1$-$C_6$ alkoxy, an amino acid or a peptide residue;
$R_2$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, or phenylalkyl where the alkyl portion is straight or branched chain alkyl having 1-6 carbon atoms, or a group of the formula

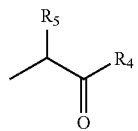

$R_5$ represents hydrogen or an amino acid side chain; and
$R_4$ is hydroxy, $C_1$-$C_6$ alkoxy, an amino acid or peptide residue; or
$NR_1R_2$ forms a nitrogen heterocycle; and
$R_3$ is an amino acid or a peptide residue.

These substrates can be prepared as described in U.S. Pat. No. 5,399,437. Suitable substrates include the following: D-FPR-(cyclohexyl)ANSN (where FPR represents Phe-Pro-Arg, ANSN represents aminonaphthalenesulfonamide, $R_1$ is cyclohexyl and $R_2$ is hydrogen); D-FPR-(ethyl)ANSN ($R_1$ is ethyl and $R_2$ is hydrogen), D-FPR-(n-propyl)ANSN ($R_1$ is n-propyl and $R_2$ is hydrogen), D-FPR-(n-butyl)ANSN ($R_1$ is n-butyl and $R_2$ is hydrogen), D-FPR-(n-hexyl)ANSN ($R_1$ is n-hexyl and $R_2$ is hydrogen), D-FPR-(benzyl)ANSN ($R_1$ is benzyl and $R_2$ is hydrogen), D-FPR-(hexamethylene)ANSN ($NR_1R_2$ represents an azepan-1-yl group), D-FPR-(isopropyl)ANSN ($R_1$ is isopropyl and $R_2$ is hydrogen), D-FPR-(methoxyethylene)ANSN ($R_1$ is methoxyethyl and $R_2$ is hydrogen), D-FPR-(t-butyl)ANSN ($R_1$ is t-butyl and $R_2$ is hydrogen), D-FPR-(methylacetate)ANSN ($R_1$ is —$CH_2CO_2CH_3$ and $R_2$ is hydrogen), D-FPR-(di-ethyl)ANSN ($R_1$ and $R_2$ are both ethyl), Boc-D-FPR-(cyclohexyl)ANSN ($R_1$ is cyclohexyl and $R_2$ is hydrogen), (p-F)FPR-(ethyl)ANSN ($R_1$ is ethyl and $R_2$ is hydrogen), Boc(p-F)FPR-(ethyl)ANSN ($R_1$ is ethyl and $R_2$ is hydrogen), D-FVR-(ethyl)ANSN ($R_1$ is ethyl and $R_2$ is hydrogen), Boc-D-FVR-(ethyl)ANSN ($R_1$ is ethyl and $R_2$ is hydrogen), D-LPR-(propyl)ANSN ($R_1$ is propyl and $R_2$ is hydrogen), Boc-D-LPR-(propyl)ANSN ($R_1$ is propyl and $R_2$ is hydrogen), D-VPR-(butyl)ANSN ($R_1$ is n-butyl and $R_2$ is hydrogen), Boc-D-VPR-(butyl)ANSN ($R_1$ is n-butyl and $R_2$ is hydrogen), L-VPR-(butyl)ANSN ($R_1$ is n-butyl and $R_2$ is hydrogen), Boc-L-VPR-(butyl)ANSN ($R_1$ is n-butyl and $R_2$ is hydrogen), D-VLR-(butyl)ANSN ($R_1$ is n-butyl and $R_2$ is hydrogen), Boc-D-VLR-(butyl)ANSN ($R_1$ is n-butyl and $R_2$ is hydrogen), L-VLR-(butyl)ANSN ($R_1$ is n-butyl and $R_2$ is hydrogen), Boc-L-VLR-(butyl)ANSN ($R_1$ is n-butyl and $R_2$ is hydrogen), D-LSR-(propyl)ANSN ($R_1$ is propyl and $R_2$ is hydrogen), Boc-D-LSR-(propyl)ANSN ($R_1$ is propyl and $R_2$ is hydrogen), D-FLR-(propyl)ANSN ($R_1$ is propyl and $R_2$ is hydrogen), Boc-D-FLR-(propyl)ANSN ($R_1$ is propyl and $R_2$ is hydrogen), L-FLR-(propyl)ANSN ($R_1$ is propyl and $R_2$ is hydrogen), D-VSR-(isopropyl)ANSN ($R_1$ is isopropyl and $R_2$ is hydrogen), Boc-D-VSR-(isopropyl)ANSN ($R_1$ is isopropyl and $R_2$ is hydrogen), D-LGR-(cyclohexyl)ANSN ($R_1$ is cyclohexyl and $R_2$ is hydrogen), Boc-D-LGR-(cyclohexyl)ANSN ($R_1$ is cyclohexyl and $R_2$ is hydrogen), D-PFR-(isopropyl)

ANSN ($R_1$ is isopropyl and $R_2$ is hydrogen), and Mes-D-LGR (di-ethyl)ANSN ($R_1$ and $R_2$ are both ethyl). A preferred substrate is D-FPR-(cyclohexyl)ANSN.

In addition to fluorogenic substrates, chromogenic substrates such as p-nitroaniline-based (pNA-based) substrates may be employed.

Tissue factor from a variety of sources and species can be assayed using the invention. Preferably, the TF to be assayed with the invention is human TF. There are several sources for human TF. The sources include brain tissue, placenta, endothelial cells, tissue extract, plasma, cell extract, synthetic or naturally derived thromboplastin, and recombinant human TF. The fVIIa used in the TF assay is preferably either native human factor VIIa or recombinant factor VIIa, although factor VIIa from other species and sources may be employed.

The concentration of TF in the sample can be determined by quantifying the TF-dependent enzymatic activity of the TF/fVIIa complex. This involves comparing the TF-dependent enzymatic activity to a standard calibration curve. Quantifying the TF-dependent enzymatic activity of the TF/fVIIa complex in a sample with known concentrations of TF generates the standard curve. The concentrations of TF used for creating the standard curve may range from about 0.1 pM to about 1 mM, as long as factor VIIa is maintained in a molar concentration greater than that of TF, i.e., in excess relative to the TF molar concentration.

The specificity, sensitivity and limits of detection of the tissue factor assay may be modulated by employing techniques to physically capture tissue factor from the sample solution. This may be accomplished by, for example, using immunocapture techniques that employ immobilized anti-tissue factor antibodies or by immobilizing the enzyme (factor VIIa) itself. Using such techniques, tissue factor can be captured or removed from solution while extraneous materials are washed away. Techniques suitable for adhering antibodies to assay plates are well-known in the art as are methods for immobilizing enzymes such as fVIIa. Suitable anti-tissue factor antibodies are commercially available or may be prepared using methods known in the art.

The performance of the tissue factor assay can be enhanced if desired by adjusting various assay conditions. For example, the pH and ionic strength of the assay buffer can be adjusted.

The second aspect of the invention is a method used to determine the fVIIa enzymatic activity in a sample, preferably a fluid sample, suspected of containing fVIIa or containing an unknown quantity of fVIIa.

As noted above, the term "determine" as used herein encompasses both quantitative measurements as well as qualitative assessments. Thus, the methods of the invention can be used to determine (1) if any fVIIa is present in a sample and (2) the amount of fVIIa activity in a sample.

The assay in the second aspect first involves combining TF and fVIIa to form a TF/fVIIa complex, i.e., a reaction mixture. Optionally, added to the reaction mixture are divalent metal ions, such as calcium ion, or metal ion chelators, such as ethylenediamimetetraacetic acid (EDTA) and ethylene glycol-bis(2-aminoethylether)-N,N,N',N'-tetraacetic acid (EGTA). Other optional components of the reaction mixture include alcohols and polyhydroxylated materials. Representative alcohols include lower alcohols, e.g., $C_1$-$C_6$ alcohols such as methanol, ethanol, propanol, pentanol, and hexanol. Polyhydroxylated materials include various glycols and sugars. Representative polyhydroxylated materials include glycerol, ethylene glycol, diethylene glycol, triethylene glycol, propylene glycol, dipropylene glycol, trimethylene glycol, butylene glycols, 1,2-cyclohexanediol, poly(oxyalkylene)p-olyols derived from the condensation of ethylene oxide, propylene oxide, or any combination thereof, 1,1,1-trimethylol-propane, 1,1,1-trimethylolethane, 2,2-dimethyl-1,3-propane diol, and pentaerythritol. More preferably, the alcohol is ethanol or n-propanol. Preferred polyhydroxylated materials include glycerol, ethylene glycol, and propylene glycol. More preferably, the polyhydroxylated material is ethylene glycol or propylene glycol.

Factor VIIa from a variety of sources and species can be assayed using the methods of the invention. Preferably, the fVIIa to be assayed is human factor VIIa. Possible sources include plasma, tissue extract, cell extract or recombinant material. Preferably, the TF used in the fVIIa assay is native human tissue factor or recombinant human tissue factor, although TF from other sources may be employed. Possible sources of TF also include synthetic or naturally derived thromboplastin.

The concentration of fVIIa in the sample can be found by quantifying the fVIIa-dependent enzymatic activity of the TF/fVIIa complex. This involves comparing the fVIIa dependent enzymatic activity to a standard calibration curve. Quantifying the fVIIa-dependent enzymatic activity of the TF/fVIIa complex in a sample with known concentrations of fVIIa generates the standard curve. The concentrations of fVIIa used for creating the standard curve may range from about 0.1 pM to about 1 mM, so long as TF is maintained in a molar excess over the factor VIIa.

When developing a calibration curve, there is a possibility that TF may not be present in an excess relative to the concentration of fVIIa. If so, there will be no change in the fluorescence level with change in concentration, i.e., a flat line will be generated, until the fVIIa concentration is reduced to a point where TF is in excess. Preferably, the excess of TF is about a 2-fold excess; alternatively, the molar excess of TF is about a 100-fold molar excess; in another alternative, the excess of TF is about a 1000-fold excess.

Enzymatic activity of the complex may be determined in a manner similar to that used to assay for TF.

The specificity, sensitivity and limits of detection of the basic factor VIIa assay described above may be enhanced by employing techniques to physically capture factor VIIa from the sample solution. This may be accomplished using immunocapture techniques that employ immobilized anti-factor VIIa antibodies or by immobilizing the cofactor (tissue factor) itself. In this manner, factor VIIa may be captured from solution while extraneous materials are washed away in subsequent steps The performance of the factor VIIa assay can be enhanced if desired by adjusting various assay conditions. As with the TF assay, for example, the pH and ionic strength of the assay buffer can be adjusted.

This invention is illustrated further by the following examples, which are not to be construed as limiting the invention in scope or spirit to the specific compounds or procedures described in them.

Example 1

Varying concentrations of fVIIa (0-1000 pM) were incubated with 5 nM TF in 20 mM Hepes (N-2-hydroxyethylpip-erazine-N'-2-ethanesulfonic acid), 0.15 M Sodium Chloride (NaCl), pH 7.4 (HBS), containing 20 mM EDTA for 10 minutes at room temperature, followed by the addition of 100 µM D-FPR-(cyclohexyl)ANSN. Substrate hydrolysis was monitored continuously for five minutes in a fluorometer at an excitation wavelength of 350 nm and an emission wavelength of 470 nm. The rates of substrate hydrolysis were determined for each fVIIa concentration tested. FIG. 1 is a graph of a calibration line based on these rates of hydrolysis at various factor VIIa concentrations. FIG. 1 shows that the factor VIIa/TF dependent rate of substrate hydrolysis is linear over the range of factor VIIa concentrations tested.

Example 2

Normal citrated plasma was diluted (1:1) with HBS containing 20 mM EDTA, and the pH was adjusted to 7.4. Five nM TF was then added. The plasma was incubated for 10 minutes at room temperature followed by the addition of 100 µM D-FPR-(cyclohexyl)ANSN. The rates of substrate hydrolysis were determined. In a control experiment, the rate of substrate hydrolysis was evaluated for the same plasma sample, but in the absence of TF. The increased rate of substrate hydrolysis observed in the presence of TF (versus the control) was attributed to the activity of the factor VIIa/TF complex. The results were compared to the FIG. 1 calibration curve. The plasma sample yielded a fVIIa concentration of 102 pM.

Example 3

Figure 2:
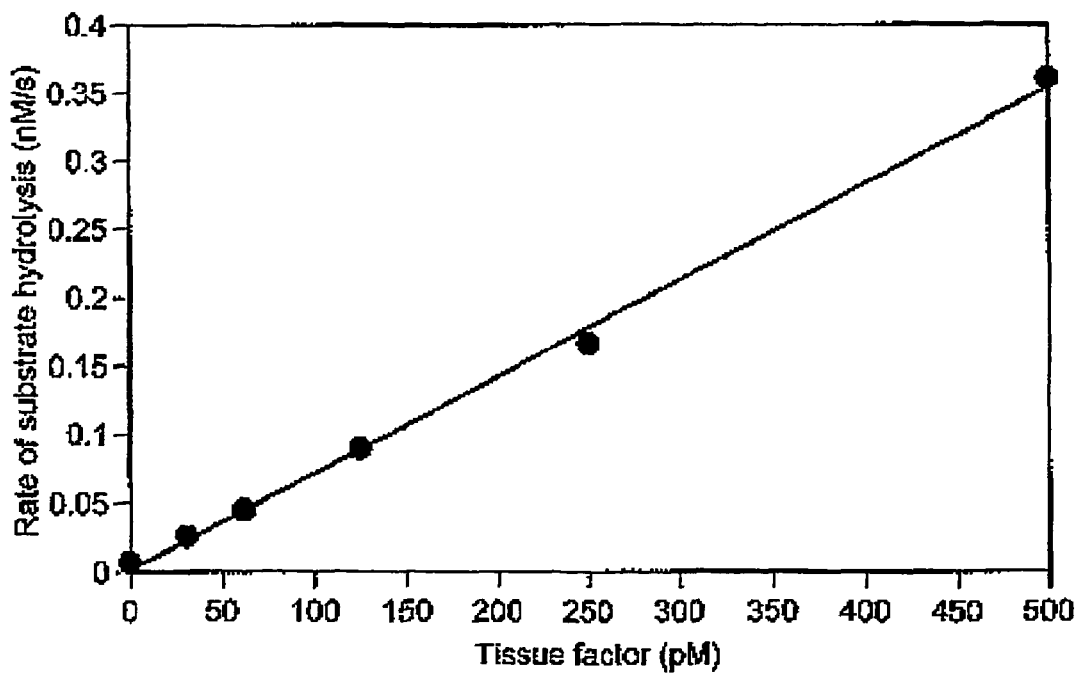
FIG. 2 is a fluorogenic assay calibration curve for TF cofactor activity in the presence of excess (2 nM) factor VIIa.

Concentrations of TF were varied (0-500 pM) and incubated with 2 nM fVIIa in HBS pH 7.4, containing 2 mM Calcium Chloride ($CaCl_2$), for 10 minutes at room temperature. Next, 50 µM D-FPR-(n-butyl)ANSN was added. Substrate hydrolysis was then monitored continuously for five minutes in a fluorometer at an excitation wavelength of 350 nm and an emission wavelength of 470 nm. The rates of substrate hydrolysis were determined for each TF concentration tested. The rate of hydrolysis by 2 nM fVIIa alone was measured and subtracted from the rates observed in the presence of TF. FIG. 2 is a graph of a calibration line based on these rates of hydrolysis at various TF concentrations. FIG. 2 shows that the factor VIIa/TF dependent rate of substrate hydrolysis is linear over the range of TF concentrations tested.

Example 4

In this example the preparation for TF employed in Example 3 was relipidated into phospholipid (PCPS) vesicles, composed of 75% phosphatidylcholine (PC) and 25% phosphatidylserine (PS). Relipidated TF, 250 pM TF to 500 nM PCPS, was incubated with 2 nM fVIIa in HBS, 2 mM $CaCl_2$ pH 7.4 for ten minutes at room temperature. Next, 50 µM D-FPR-(n-butyl)ANSN was added. Rates of hydrolysis were determined and the rate of hydrolysis by 2 nM fVIIa alone was measured and subtracted from the rates observed in the presence of TF. The net rate of hydrolysis was then compared to the FIG. 2 calibration curve. The assay data indicates that 35-40% of the TF added to the relipidation mixture was expressed as functional TF, which indicates poor recovery of total TF activity following relipidation.

Example 5

Figure 3:
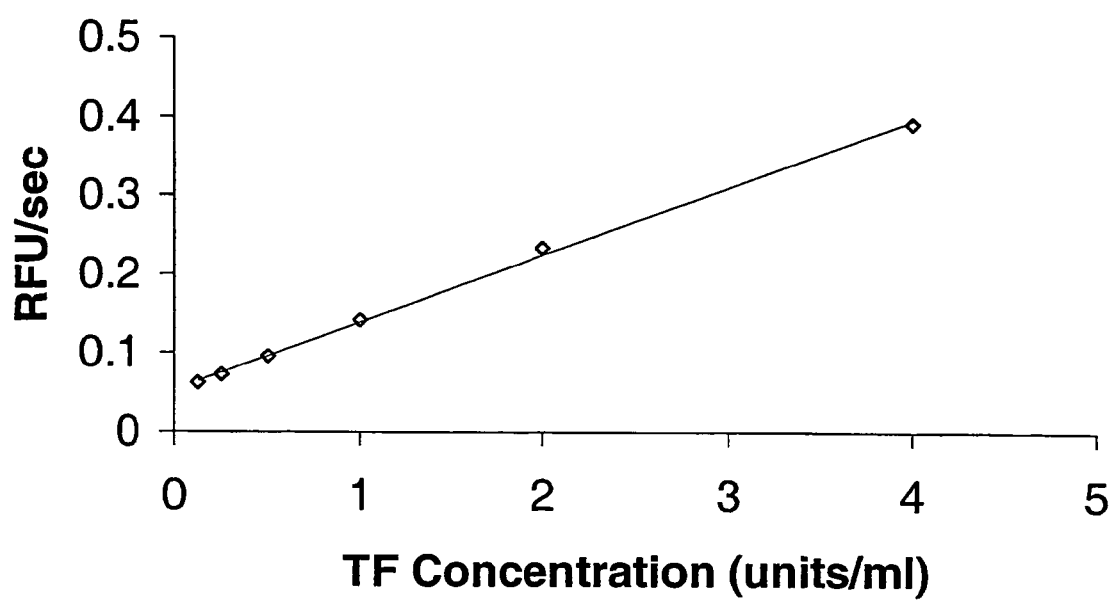
FIG. 3 is a calibration curve for TF activity where TF activity is expressed as the amount of cofactor activity per milliliter of solution (units/ml). RFU represents relative fluorescent units.

A standardized preparation of recombinant human TF with a cofactor activity of 241 units/ml (specific activity of 3906 units/milligram) was serially diluted to create stock assay standards in the range of 8 to 0.25 units/ml. One hundred microliters of each stock standard was combined with 50 microliters of 120 nM factor VIIa. Subsequently 50 microliters of 150 uM D-FPR-(n-butyl)ANSN was added and the rate of substrate hydrolysis was measured in a fluorometer at an excitation wavelength of 350 nm and an emission wavelength of 470 nm. A standard curve was generated in FIG. 3 by plotting the change in fluorescent intensity over time versus the concentration of TF (in units/ml). In a similar manner, a sample of TF (0.8 mg/ml) with an unknown amount of cofactor activity was assayed for comparison to the standard. After correcting for assay dilution, the unknown sample returned an assay value of 2803 units per milliliter, and thus a specific activity of 3504 units per milligram. Consequently, this allows for comparison of different preparations of TF using their specific activity, which is a direct indication of quality and functionality.

Example 6

Varying concentrations of fVIIa (0-200 pM) were incubated with 40 nM nM TF, in a buffer of 20 mM Hepes (N-2-hydroxyethylpiperazine-N'-2-ethanesulfonic acid), 0.05 M Sodium Chloride (NaCl), pH 8.0 (HBS), containing 0.1% (w/v) polyethlyeneglycol (PEG) and 25% (v/v) ethylene glycol for 10 minutes at room temperature, followed by the addition of 80 µM D-FPR-(cyclohexyl)ANSN. Substrate hydrolysis was allowed to proceed for 24 hours at room temperature after which an endpoint reading was taken in a fluorometer at an excitation wavelength of 350 nm and an emission wavelength of 470 nm. When a calibration curve was constructed by plotting the relative fluorescence intensity versus factor VIIa concentration, a linear relationship was observed with the lower limit of detection being approximately 2 pM. In this case, the optimized buffer conditions (pH, ionic strength, and additives) along with an extended assay period and end-point reading yielded a lower limit of detection that was 20 fold lower than that observed using the standard assay conditions outlined in "example 1".

Example 7

A microtiter assay plate was precoated with purified recombinant tissue factor and residual plate binding sites were blocked with bovine serum albumin using conventional coating and blocking methods. Serial dilutions of factor VIIa in TBS, pH 7.4 (20 nM to 8.5 pM) were added to the plate and allowed to incubate for 2 hours at room temperature. The plate was then washed with TBS, pH 7.4 to remove non-bound factor VIIa and this was followed by the addition of 80 µM D-FPR-(cyclohexyl)ANSN. Substrate hydrolysis was allowed to proceed for 24 hours at room temperature after which an endpoint reading was taken in a fluorometer at an excitation wavelength of 350 nm and an emission wavelength of 470 nm. When a calibration curve was constructed by plotting the relative fluorescence intensity versus factor VIIa concentration, a linear relationship was observed with the lower limit of detection being approximately 8.5 pM.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the invention as set forth in the claims. To particularly point out and distinctly claim the subject matter regarded as invention, the following claims conclude this specification.

What is claimed is:

1. A method for determining the concentration of tissue factor (TF) in a sample suspected to contain TF, comprising: (a) combining the sample and a molar excess of factor VIIa (fVIIa) compared to the moles of TF in the sample to produce a TF/fVIIa enzyme complex; (b) detecting the enzymatic activity of the complex using a fluorogenic or chromogenic substrate; (c) generating numerical values correlated with the enzymatic activity of the sample; and (d) comparing the numerical values with a standard curve of TF-dependent enzymatic activity, wherein the standard curve is generated by quantifying TF-dependent enzymatic activity of the TF/fVIIa complex in samples with known concentrations of TF.

2. The method of claim 1, wherein the substrate is a compound of the formula:

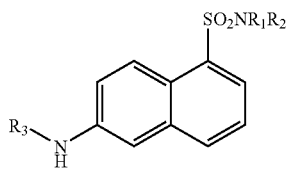

or a pharmaceutically acceptable non-toxic salts thereof; wherein $R_1$ is hydrogen, straight or branched chain lower alkyl having 1-6 carbon atoms optionally substituted with $C_1$-$C_6$ alkoxy, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula:

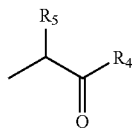

$R_5$ represents hydrogen or an amino acid side chain; and
$R_4$ is hydroxy, C1-C6 alkoxy, an amino acid or a peptide residue;

$R_2$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, or phenylalkyl where the alkyl portion is straight or branched chain alkyl having 1-6 carbon atoms, or a group of the formula:

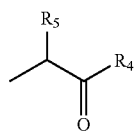

$R_5$ represents hydrogen or an amino acid side chain; and
$R_4$ is hydroxy, C1-C6 alkoxy, an amino acid or peptide residue; or
$NR_1R_2$ forms a nitrogen heterocycle; and
$R_3$ is an amino acid or a peptide residue.

3. The method of claim 1, where the substrate is a chromogenic substrate.

4. The method of claim 3, wherein the chromogenic substrate is a para-nitroaniline based substrate.

5. The method of claim 1, wherein the TF is native human tissue factor.

6. The method of claim 1, wherein the sample is obtained from is brain tissue, placenta, endothelial cells, tissue extract, plasma, cell extract, synthetic or naturally derived thromboplastin, or recombinant human tissue factor.

7. The method of claim 1, wherein the fVIIa is native human factor VIIa or recombinant factor VIIa.

8. The method of claim 1, wherein the TF and the fVIIa are not of human origin.

9. The method of claim 1, wherein the concentration of TF is from 0.1 pM to 1 mM.

10. The method of claim 1, wherein the reaction mixture contains divalent metal ion or a metal ion chelator.

11. The method of claim 10, wherein the divalent metal ion is calcium ion, magnesium ion or manganese ion.

12. The method of claim 10, wherein the metal ion chelator is ethylenediamimetetraacetic acid (EDTA) or ethylene glycol-bis(2-aminoethylether)-N,N,N',N'-tetraacetic acid (EGTA).

* * * * *

UNITED STATES PATENT AND TRADEMARK OFFICE
CERTIFICATE OF CORRECTION

PATENT NO. : 7,604,932 B2 Page 1 of 1
APPLICATION NO. : 10/534187
DATED : October 20, 2009
INVENTOR(S) : Jenny et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 688 days.

Signed and Sealed this

Fifth Day of October, 2010

David J. Kappos
*Director of the United States Patent and Trademark Office*